United States Patent [19]

Kumar et al.

[11] Patent Number: 5,624,850
[45] Date of Patent: Apr. 29, 1997

[54] IMMUNOASSAYS IN CAPILLARIES

[75] Inventors: Amit Kumar, Sacramento; Shanta Kharadia, Santa Clara; Marcos Piani, Redwood City; Sudhir Deshpande, Santa Clara; Richard Rocco, Sunnyvale, all of Calif.

[73] Assignee: Idetek, Inc., Sunnyvale, Calif.

[21] Appl. No.: 254,302

[22] Filed: Jun. 6, 1994

[51] Int. Cl.$^6$ .......... G01N 33/02; G01N 33/552; G01N 21/00; G01N 15/06
[52] U.S. Cl. .......... 436/527; 436/20; 436/23; 436/172; 436/538; 422/57; 422/68.1; 422/82.07; 422/82.08
[58] Field of Search .......... 436/518, 524, 436/527, 536, 538, 541, 20, 23, 56, 164, 172, 800, 805, 824; 422/55, 57, 61, 68.1, 74, 82.07, 82.08, 312; 435/809, 810, 968, 971, 972

[56] References Cited

U.S. PATENT DOCUMENTS

| | | | |
|---|---|---|---|
| 4,116,638 | 9/1978 | Kenoff | 422/99 |
| 4,299,916 | 11/1981 | Litman et al. | 436/6 |
| 4,590,157 | 5/1986 | Chandler et al. | 435/7 |
| 4,844,869 | 7/1989 | Glass | 422/68 |
| 4,909,990 | 3/1990 | Block et al. | 422/82.11 |
| 5,009,998 | 4/1991 | Chou et al. | 435/7.92 |
| 5,152,962 | 10/1992 | Lackie | 422/681 |
| 5,164,598 | 11/1992 | Hillman et al. | 250/341 |

OTHER PUBLICATIONS

"Optical biosensors for immunoassays: the fluorescence capillary–fill device," by R. A. Badley, et al., Phil. Trans. R. Soc. Lond. B 316, 143–160 (1987).

"A rapid quantitative capillary tube enzyme immunoassay for human chorionic gonadotropin in urine," by P.A. Nagainis, et al., Clinica Chimica Acta, 160 (1986) 273–279.

"A new enzyme immunoassay system suitable for field use and its application in a snake venom detection kit," by H.M. Chandler, et al., Clinica Chimica Acta, 121 (1982) 225–230.

"A rapid semi quantitative capillary enzyme immunoassay for digoxin," by K. Healey, et al., Clinical Acta, 134 (1983) 51–58.

*Primary Examiner*—James C. Housel
*Assistant Examiner*—Jennifer Shaver
*Attorney, Agent, or Firm*—Lyon & Lyon LLP

[57] ABSTRACT

Immunoassay methods employing capillary containers are provided. The immunoassays may be competitive or sandwich immunoassays, where fluorescently labeled conjugates are used. Sample suspected of containing analyte is combined with fluorescently labeled conjugate, as well as any additional reactants which may be required. At least a portion of the incubated sample is placed in a capillary container. The capillary container has, on at least one region of its inner surface, a binding member capable of complexing with the fluorescently labeled conjugate, either directly or indirectly. Fluorescently labeled conjugate not complexed to binding member is then washed from the capillary container. The complexed fluorescently labeled conjugate is detected by irradiating the capillary and measuring the emitted signal. The intensity of the emitted signal is indicative of the presence of analyte in the sample.

14 Claims, No Drawings

IMMUNOASSAYS IN CAPILLARIES

TECHNICAL FIELD

The field of this invention is analyte detection by immunoassay.

BACKGROUND

Many situations exist where qualitative and quantitative detection of the presence of an analyte in a sample is desired. Situations where analyte detection is desirable arise in diverse industries, including: 1) the health care industry, e.g. in clinical and diagnostic medicine; 2) the food processing and chemical industries, e.g. in quality control for food production; and 3) the environmental control industry, e.g. monitoring for the presence of various pollutants in air, ground water or soil.

Many devices and protocols which detect the presence of analytes through chemical and physical means have been developed. Immunoassays make up one broad field of assays which find use in the detection of analytes. In immunoassays, the occurrence of binding events between specific binding pair members is used as an indication of the presence of analyte in the sample. Benefits of using immunoassays in analyte detection include high sensitivity, high specificity, reliability and short assay times.

The binding events which are detected in immunoassays often occur at the surface of a solid support. The time required for a particular immunoassay will depend on the ability of free reactants in the assay medium to reach and bind to the support surface. The ability of the free reactants to reach reactant on the support surface is dependent on many factors including the concentration of reactant on the surface of the support and the surface to volume ratio of the sample support combination. One method of decreasing the time required for an immunoassay is to use a higher concentration of bound reactant on the support surface. Another approach is to increase the ratio of the surface area of the support compared to the volume of sample assayed.

Toward this end, one type of immunoassay which has been demonstrated in capillaries is the ELISA immunoassay. Conventionally, ELISA assays have been conducted in microtiter plates consisting of wells. In ELISA immunoassays, binding events of interest are detected through the appearance of detectable product produced by an enzyme. The formation of a detectable product can be amplified to the extent required by increasing the concentration of the substrate and/or increasing the reaction time. Therefore, there is the opportunity to greatly increase the signal with only a few enzymes becoming bound.

With ELISA immunoassays conducted in capillaries, rapid quantitative results are reported. The reported ELISA assays are described as sensitive and able to detect small amounts of analyte. See Nagianis et al., "A Rapid Quantitative Capillary Tube Enzyme Immunoassay for Human Chorionic Gonadotropin in Urine," Clin. Chem. Acta (1986) 273–279. However, there are disadvantages inherent in ELISA assays. In ELISA immunoassays, a multistep protocol is required using measured reagents. The steps include sample addition, enzyme conjugate addition, incubation, substrate addition, and washing steps. This multiplicity of procedural steps increases the probability of error in the overall assay procedure, particularly when the result may be substrate concentration and/or time sensitive. Also, enzyme reactions tend to be temperature sensitive, which requires temperature control. In addition, the enzyme label is not directly detectable. Instead, one must allow for the detectable product to be produced. Further, ELISA protocols may not be suited for all assays on all types of liquids, where the liquid comprising the analyte of interest may also contain contaminants which interfere with one or more individual steps in the assay, e.g. enzyme activity, detectability of enzyme product, and the like.

Thus, interest exists in the development of assays requiring simple protocols, a minimum of required measurements and small sample volumes, where the assays are relatively insensitive to variations from an optimized protocol, as well as variations in ambient conditions.

Relevant Literature

U.S. Pat. Nos. 5,204,525; 5,164,598; 5,144,139; 5,140,161; 5,004,923; 4,963,498; 4,948,961; 4,756,884 describe combining a sample with reagents, introducing the sample into capillaries, and measuring various agglutination events in the capillaries.

U.S. Pat. Nos. 4,844,869; 4,909,990 and 5,152,962 describe an immunoassay apparatus having an optical fiber inside a hollow tube, where the space between the fiber and tube holds a volume of sample to be assayed. Binding events occur on the surface of the optical fiber and are indicative of the presence of analyte in the sample being assayed. The binding events are detected through changes in total internal reflection of light in the optical fiber.

Other references of interest include: Nagianis et at., Clinica Chimica Acta (1986) 160:273–279; Badley et al., Phil. Trans R. Soc. Lond. (1987) 316: 143–160; Healey et al., Clinica Chimica Acta (1983) 134: 51–58; and Chander & Hurrell, Clinica Chimica Acta (1982) 121:225–230.

Hagamuchi et al., J. Eur. Biochem. (1976) 71: 459–467, describes the preparation of capillary tubes for use in ELISA immunoassays.

SUMMARY OF THE INVENTION

Immunoassay methods are provided for detecting the presence of at least one analyte in a sample employing a capillary container. Both competitive and sandwich immunoassays may be employed with a fluorescently labeled reactant. In the subject method, sample suspected of comprising analyte is combined with a fluorescer labeled conjugate and a capture specific binding member reagent bound to the internal wall of a capillary in at least a detection region, as well as any additional reactants which may be required by a particular immunoassay format. After sufficient time for forming complexes between the binding member and fluorescent labeled conjugate, unbound labeled conjugate is washed from the capillary. The amount of labeled conjugate bound to the capture binding member reagent is then detected by first irradiating the capillary and then measuring the resultant fluorescent signal. The intensity of the fluorescent signal is indicative of the presence of analyte in the sample.

DESCRIPTION OF THE SPECIFIC EMBODIMENTS

Immunoassay methods are provided for the detection of at least one analyte in a sample employing capillary containers. In the subject methods, sample suspected of comprising analyte is combined with a fluorescently labeled conjugate and a capture specific binding member bound to the internal wall of a capillary in at least a detection region. The combining may be stepwise rather than concurrent, where the sample and conjugate may be combined first or the sample and capture reagent combined first. The complexed labeled conjugate is detected by irradiating the capillary at the detection region and detecting the resultant fluorescent signal.

In further describing the subject invention, capillary containers that may find use in the subject method will be discussed first. After the capillary containers have been described, the subject method will be developed in greater detail.

A wide variety of capillary containers designed for diverse uses are known in the art. Many of these capillary containers are suitable for use in the subject invention. Generally, capillary containers used in the subject method should be translucent, so that irradiation light and fluorescence emissions are efficiently transmitted across the capillary wall. Materials from which suitable capillaries may be formed include glasses, such as soft glass and silicate glass, fused silica and plastics, such as polystyrene, polyethylene, and the like. The significant factor is that the wall should not interfere with the efficient passage of light at the wavelengths of interest, namely the excitation light and emitted light.

Capillary containers suitable for use in the subject invention may have a wide variety of dimensions, as long as liquid media are efficiently drawn up by capillary force. The capillaries may have cross sections which are circular, square, rectangular, oval or the like. Typically, the capillaries will have circular cross-sections. The inner diameters of suitable capillaries may range from about 0.1 µm to 1 mm, usually about 0.3 µm to 1.0 mm and more usually about 0.50 µm to 1 mm. The length of suitable capillaries will typically be at least about 10 mm, usually at least about 15 mm, more usually at least about 50 mm, or longer. The surface of capillary may be enhanced to increase binding affinity. For glass, to enhance binding of proteins to the glass, the surface may be modified to provide cationic groups, such as amines on the surface to enhance the binding affinity of the protein to the surface. Conveniently, aminoalkylsiloxanes may be used, which are conventional coating agents, where the aminoalkyl group is of from about 2 to 6 carbon atoms and the alkoxy groups are of from about 1 to 6 carbon atoms.

At least one region of the inner surface of the capillary will be coated with the capture binding member, the detection region, where the capture binding member binds directly or indirectly through an intermediate binding agent to the fluorescent labeled conjugate. Depending on the particular method used to coat the capillary, this region may encompass the entire inner surface of the capillary or may be limited to a portion of the inner surface of the capillary. The region of the inner surface comprising binding member will typically range from about 10 to 100% of the inner surface, and will usually range from about 30 to 80% of the inner surface. Conveniently, the entire capillary, or one end thereof, may be immersed in the coating media to be coated. When immersed at one end, the coating medium may be brought up into the capillary by any suitable means, e.g. by capillary force, conveniently to a predetermined height, which may be indicated by a scoring or other designation on the capillary. Alternatively, the liquid could be pumped into a portion or the whole length of the capillary. This means that all or a portion of the external surface may be coated with the capture binding member. Since this method of coating is economical and convenient, a protocol for this embodiment will be specifically described.

Depending on the particular immunoassay used in the subject method, a variety of agents may serve as the binding members. In general, the binding members should complex or bind to their complementary binding pair members in the subject assays with sufficient affinity to withstand wash procedures used in the subject method. Typically, the affinity between the binding member and its complementary binding pair will be at least about $10^6$/mol, frequently at least about $10^8$/mol or higher. The binding member will complex directly or indirectly to the fluorescently labeled conjugate. For example, in a competitive immunoassay format, the binding member will bind directly to the labeled conjugate. In a sandwich assay format, the binding member will complex to the labeled conjugate indirectly through the analyte. Illustrative binding members include receptors, such as antibodies and binding fragments thereof, e.g. F(ab) and F(ab)$_2$ fragments, enzymes, lectins, etc. . . . ; ligands, such as antigens, haptens or other reciprocal binding members; and conjugates comprising ligands and receptors, bonded to the fluorescent label.

Instead of coating a region with a single binding member, the inner surface of the capillary may comprise two or more binding members at the same or different sites. In this situation, each different binding member will be involved in the detection of a different analyte in the sample, where, when the binding members are at the same site, the fluorescent label associated with each analyte can be independently determined, e.g. different emission maximum wavelength, at least about 2 nm different, and/or different delay time for emission. Thus, one could assay for a multiplicity of analytes simultaneously.

In coating the internal wall of the capillary containers for use in the subject method, capillaries will be contacted with a solution comprising the binding member. For coating the inner capillary surface with the binding member solution, a variety of techniques may be employed, depending in part on the nature of the capture binding member and the nature of the internal wall. With most proteins, particularly antibodies, albumins and globulins, the proteins will stick to the wall without covalent bonding and be stably maintained under the conditions of the assay. The capillary may be entirely submerged in the capture binding member solution. Alternatively, only a portion of the capillary may be coated with the binding member solution, e.g. by dipping one end of the capillary in the solution and allowing the solution to rise only a portion of the length of the capillary tube. To prevent the presence of binding members on the outer wall, the outer wall may be washed thoroughly, before allowing the coating solution to dry on the surface, the external wall may be coated with a hydrophobic coat, e.g. TEFLON®, or other procedure.

In preparing the subject capillary containers, as indicated for proteins above, it may be sufficient to contact capillaries with untreated surfaces to a solution comprising the binding reagent. The binding solution will usually be a buffered solution having from about $10^{-7}$ to $10^{-3}$ g protein/ml. For the most part, the protein binding member will be an antibody or fragment thereof. Methods of stably coating glass and plastic surfaces are well known. See Harlowe & Lane, Antibodies: A laboratory manual, Cold Spring Harbor Laboratory, Cold Spring Harbor, N.Y. (1988). In many instances, where the binding member is not a protein, it may be conjugated to a protein, leaving the binding site available for binding to the complementary member. For example, haptens may be conjugated to a protein which will not interfere with the assay and the protein conjugate used in the binding solution. In this way a non-binding analyte or mimetic thereof may be directly bound to the internal surface of the capillary without having to functionalize the surface to provide covalent binding of the non-binding analyte or mimetic thereof. However, in many instances it may be desirable to coat the inner surface with an agent which enhances the binding of the protein to the surface, such as amino groups.

Where the binding member does not provide for stable binding, the inner surface of the capillary may be activated or functionalized to provide covalent binding of the binding member to the capillary surface. The particular technique used in treating the capillary surface will depend on the composition of the capillary and the binding member, e.g. the functional groups available on the binding member for reaction. For treating the surfaces of glass capillaries, silanization may find use, where the specific binding pair members comprise suitable functional groups, e.g. amino, carboxy, sulfonyl, thiol, activated olefin, such as maleimido, etc. . . . . With other surfaces, such as plastics, e.g. polystyrene and polyethylene, the surface can be functionalized to provide for reactive amino, carboxy, thio, sulfonyl, hydroxy or other functional groups, by acylation, nitration and reduction, oxidation with ozone, chlorosulfonation, and the like. The specific functional group provided on the capillary surface will depend on the binding member. If the binding member does not naturally comprise a useful available functional group, the binding member may be modified, so as to provide for a functional group that will react with the activated surface, e.g. amino with carboxy, thiol with activated olefin, hydroxy with an activated halogen, and the like.

After the binding member has been bound to the surface of the capillary, non-specific active sites or "hot spots" may remain on the capillary surface. These active sites must be occupied or blocked prior to use of the capillary in the subject method. Otherwise, non-specific adsorption of the various assay reagents may occur. Non-specific adsorption should be avoided because it may result in nonspecific binding of the label to the surface. Blocking of active sites may be achieved by contacting the internal capillary surface with a wide variety of blocking solutions. Coating the capillary surface with the blocking solution may be achieved using the methods described above for coating the surface with the binding member. The blocking solution of choice will depend on the particular assay being conducted. See Harlow and Lane, Antibodies (1988) 497, supra. Illustrative blocking solutions include BLUTTO®, BLUTTO®/ TWEEN®, TWEEN®, BSA and Horse Serum.

Once the capillaries have been prepared, they may be used immediately or conveniently stored for use at a later time. When the capillaries are stored for use at a later time, they will be stored at ambient or reduced temperature conditions.

The capillary containers used in the subject invention having been described, the subject method will now be discussed in greater detail.

The subject method is suitable for the detection of analytes in samples from a variety of sources having widely different components, particularly without any significant pretreatment, other than dilution, dissolution or filtration. However in some situations the sample may need to be pre-treated prior to the assay. Where the sample is initially complex, solid or viscous, it may need to be extracted, dissolved or diluted in order to obtain a sample having the appropriate characteristics for use in the assay. Further, the sample should be one in which binding complexes formed in the subject assay are stable. Binding complexes of the subject assay will generally be stable at pH values ranging from about 5 to 9. The pH value of the sample may be adjusted, if necessary, to be about 7 by diluting with an appropriate buffer. For the most part, the samples will be liquid samples, which include food samples, e.g. milk, meat, juices,etc.; environmental samples, such as ground water, polluted liquids, such as industry discharges and physiological fluids, such as blood plasma, saliva, urine, as well as other biological fluids.

A wide range of analytes may be detected using the subject method. Detectable analytes can be any analyte capable of being recognized and bound by a specific binding pair member. The analyte may be an antigen, receptor, e.g. antibody, or hapten. Analytes of interest include naturally occurring and synthetic small organic compounds, proteins, saccharides, nucleic acids and the like. Illustrative analytes include compounds found in food, such as compounds used in the raising of domestic animals, food additives, and naturally occurring contaminants, such as antibiotics, dyes, food supplements, microorganisms and their toxins, etc.; physiologically active compounds or pathogenic markers found in physiological fluids, such as toxins, antibiotics, surface membrane proteins, cytokines, antibodies, HLA proteins, hormones, synthetic drugs, proteins of bacteria, fungi and viruses, etc.; and compounds found in the environment, such as pesticides, herbicides, organic components of waste discharges, and the like.

Depending on the type of analyte to be detected, different immunoassay formats may be employed. There is a particular immunoassay format which is preferred, which may be modified depending on the nature of the analyte, the nature of the sample, and the like. In general, immunoassays useful in the subject method are based on the formation of complexes between specific binding pair members. Common to each immunoassay used in the subject method will be an analyte, a capture binding member bound to the surface of the capillary and a fluorescent labeled conjugate.

Many different fluorescers may be employed in the subject assays. Suitable fluorescers should be capable of conjugation with antigens, haptens or antibodies in order to be used in the fluorescently labeled conjugate. The fluorescer selected will be based on synthetic convenience, emission maximum, quantum efficiency, stability under the assay conditions, and the like, but the fluorescer is not critical to the invention, so long as there is a minimum quantum yield to provide the desired sensitivity. A large number of commercially available fluorescers may be employed. Illustrative fluorescers include fluorescein isothiocyanate (FTIC), rhodamine, Texas Red, phycoerythrin and allophycoerythrin, and particularly, fluorescers that fluoresce above about 550 nm, more particularly, fluorescers that fluoresce above 600 nm, and efficiently absorb light having absorption above 500 nm, more particularly, 650 nm, such as CY-5®. The fluorescent moieties may be conjugated to form the fluorescently labeled conjugate using any convenient method. See Harlow & Lane, Antibodies (1988) pp 353–358.

Both competitive and sandwich immunoassay formats may be employed in the subject method. The particular immunoassay format employed will depend on the particular analyte characteristics, the sample characteristics, the available reagents, and the like. In competitive immunoassays, the analyte will compete with a conjugate of an analyte mimetic for binding to the reciprocal binding member, where the conjugate comprises a fluorescent label. Thus, the conjugate will have a binding site, e.g. an epitopic site, substantially the same as the analyte. In sandwich immunoassays, a conjugate is employed which has a binding member, for binding to the analyte at a site other than the site to which the capture binding member on the capillary wall binds, conjugated to a fluorescent label.

In the competitive assay, a particularly convenient protocol is where conjugate is first added to the liquid sample comprising the analyte to provide a substantially homogeneous mixture and then sample is taken up into the capillary. The conjugate may be added as a solid or preferably as a buffered solution, and as appropriate, may serve to dilute the sample and provide the appropriate pH. Generally the volume of the sample will be small, so that the reaction between the conjugate and any analyte will be rapid, frequently under 2 min, more frequently under 1 min. The capillary may then be introduced into the sample and sample drawn up by any convenient means, e.g. capillary action or active pumping, to provide an appropriately sized sample in the capillary. In the sandwich assay, the conjugate may be added to the sample as described above, or the sample may be taken up into the capillary, the sample washed from the capillary, followed by taking up a solution of the conjugate, which will bind to any analyte bound to the wall of the capillary.

With the conjugate, the complementary binding member and analyte will occupy binding sites to prevent further binding to the conjugate. Alternatively the fluorescently labeled binding member may compete directly with analyte for binding to the capture binding member on the surface of the capillary. In this format, the binding member present on the surface will be complementary to an epitopic region on the analyte. The labeled conjugate will have an analogous epitopic region which competes with the analyte in binding to the binding member on the capillary surface. In the competitive assays, the capture binding member may be a ligand, an antibody, or binding fragment thereof, analogous to or complementary to the epitope of the analyte.

In the sandwich assay, the fluorescently labeled conjugate is added to the sample and the sample drawn up into the capillary. The analyte will bind with the conjugate and the capture binding member, so that the amount of fluorescent label bound to the capillary wall will be directly proportional to the amount of analyte present.

Depending upon whether a competitive or sandwich assay is employed, and the reagents employed, the fluorescence intensity will be directly or inversely proportional to the amount of analyte in the sample. Where one is interested in a qualitative result or a semi-quantitative result, such as determining whether the amount of analyte is above a predetermined threshold, the amount of conjugate is selected to provide a clear signal as compared to the absence of analyte or analyte below the predetermined value. Thus, one may use an amount of conjugate which will be substantially absent in the detection region in the absence of analyte and provide an intense signal at the lowest concentration that one would anticipate to be encountered of analyte in the sample or vice versa.

For the most part, the subject methods will depend solely on the capillary and the conjugate for carrying out the assay. However, in some situations more complex protocols may be employed. For example, instead of having the binding member of the conjugate labeled directly, one may indirectly label the binding member. Where the binding member is an antibody, one could use a fluorescently labeled anti-antibody, so as to have a universal fluorescent reagent. One could also have a situation where one added both a fluorescently labeled conjugate and its reciprocal binding member, where the conjugate competed with the analyte for the reciprocal binding member. The capillary could then be coated with a capture binding member that captures the reciprocal binding member. For example, the reciprocal binding member could be an antibody and the capillary could be coated with Protein A or G, so as to capture all antibodies.

The subject method will generally comprise: 1) a combination step, where labeled conjugate, sample and any additional reagents are combined and the reaction allowed to proceed, 2) an introduction step for taking up at least a portion of the sample inside the capillary, 3) as required, an incubation step, where fluorescently labeled conjugate binds to the binding member on the capillary surface in relation to the amount of analyte in the sample, 4) a washing step, where the unbound labeled conjugate is removed from the capillary and, desirably, wash solution retained in the capillary, and 5) a detection step for measuring the amount of labeled conjugate remaining in the capillary.

In the first step of the subject method, sample suspected of comprising analyte and fluorescently labeled conjugate, as well as any additional reagents which may participate in the assay, are combined. The first step will be for a sufficient period of time so that the various reactants may distribute evenly throughout the sample and so that complexes between specific binding pair members, if present, may form. To aid in distribution of the reactants in the sample, the sample may be agitated during the incubation step. Although the incubation may occur at temperatures ranging from about 0° C. to 65° C, more usually from about 25° C. to 40° C., the incubation will typically occur at room temperature. The time duration of the first step will vary depending on the reaction kinetics and the temperature, usually lasting not more than about 6 hours, more usually not more than about 1 hour, and typically substantially less than 1 hour, frequently 5 minutes, even fewer than 1 minute The second step in the subject method is to introduce a portion of the incubated sample into the assay capillary. The assay sample is taken up into the capillary using any convenient means, e.g. by capillary force or active pumping, to a level which provides the desired volume. The capillary may be indexed to indicate how far the fluid meniscus goes. Generally, sample volumes introduced into the capillary will range from 2 to 20 µl, usually 5 to 15 µl, more usually 5 to 10 µl.

To avoid error as a result of the presence of binding member on the outside of the assay capillary, after taking up the sample, the capillary is turned over to move the sample away from the region which was immersed in the sample. In this situation, the capillary will have been immersed in the sample only a small portion of the length of the capillary, usually less than about 30% of the length. The sample can then be read without interference from conjugate bound to the external surface of the assay capillary.

After the sample portion has been introduced into the capillary, the sample will be incubated in a second incubation step for a sufficient time period for any complexes between members of a specific binding pairs to form. The incubation step will typically occur at room temperature, although temperatures in the range indicated above may be employed. Incubation times will typically range from about 0.5 to 2 min., usually about 0.5 to 1.5 min., and more usually about 1 min. Frequently, the time necessary for introducing the wash solution into the capillary will suffice for the incubation.

After the previous step, any labeled conjugate free in the medium is removed from the capillary. Removal of unbound labeled conjugate is conveniently accomplished through introduction of a washing fluid that displaces the sample medium comprising unbound labeled conjugate from the capillary. A variety of wash fluids may find use for the washing step. The pH of the wash fluid will be a pH in which the binding pair complexes are stable. Typically, the pH will range from 5 to 9, usually 6 to 8, and more usually about 7. Depending on the nature of the fluorescent moiety of the labeled conjugate, wash solutions which enhance the fluorescence of the labeled conjugate moiety may be employed. For example, the fluorescence of a particular fluorescent moiety may be enhanced in slightly alkaline or basic solution. In such a case, a buffer having a pH above 7 but usually less than 9 may be employed. Exemplary wash fluids include water, buffers, such as phosphate, PBS, saline solutions, carbonate buffers, and the like. The wash fluid may be introduced into the capillary using any convenient means. Usually the wash fluid will be introduced into the capillary using the same means as the means used for introduction of the sample. The wash solution may be taken up a number of times, usually not more than about 6, more usually not more than about 2, or the wash solution may be forced through the capillary using a syringe, pump or other device.

After the washing step where unbound labeled conjugate is washed from the capillary, the presence of labeled conjugate remaining on the capillary surface will then be detected in a detection step. The detection step may be conducted immediately after the wash step, or may be delayed for a period of time, if necessary. If the detection step is to be delayed, the capillaries can be stored for reasonable periods of time under ambient or reduced temperature conditions.

The detection step will usually be conducted with wash fluid in the capillary. However, if desired, the capillary may be dried prior to the detection step using any convenient drying procedure. For example, the wash fluid may be removed, followed by drying with forced air or at elevated temperatures. Usually, because drying adds an additional step to the overall assay process and is not desirable for detection, the wash fluid will be retained in the capillary.

Since fluorescent moieties are used in the labeled conjugate, detection is accomplished by first irradiating a region of the capillary comprising the detection region, followed by measuring the resultant emitted fluorescent signal. Any convenient irradiation means may be employed providing the appropriate wavelength. Exemplary irradiation means include lasers, light emitting diodes, tungsten lamps and the like. The wavelength of light used in the stimulation means will depend on the particular fluorescent moiety in the labeled conjugate. Generally, the irradiation light wavelengths will range from 300 to 900 nm, usually from about 350 to 800 nm, and more usually from about 450 to 800 nm. For example, where CY-5® is the fluorescent moiety, the wavelength of the irradiation light will range from 630 to 650 nm. The fluorescence from the fluorescent labeled conjugates present in the capillary will be measured. Measuring the emitted signal is accomplished by detecting the photons emitted in the detection region. Means for measuring fluorescence are commercially available and any convenient fluorimeter may be used. Various photodiodes, photomultipliers, and the like, may be employed, and in some instances a visual detection will suffice. For quantitation, the resultant electrical signal may be accurately measured using appropriate hardware and software. The area from which the fluorescence is measured is controlled to provide for consistent values. Controls may be employed, where the signal to concentration of the analyte is determined, so that the signal may be directly related to the concentration of analyte in the assay sample. In this manner, the presence and amount of analyte in the sample may be determined.

The following examples are offered by way of illustration and not by way of limitation.

EXPERIMENTAL

EXAMPLE 1

Preparation of a Capillary for Use in a Competitive Immunoassay to Detect Cephapirin in Milk A borosilicate glass capillary having a length of 65 mm and an inner diameter of 0.6 mm (Fisher Scientific) was washed with distilled water and then dried under a stream of air until substantially all of the distilled water had evaporated from the surfaces of the capillary. The capillary was then incubated in a 2.5% aminopropyl triethoxysilane ethanol solution for 20 min. at 80° C.

The incubated capillary was then washed with distilled water and dried in a stream of air. The dried capillary was then incubated for 2 hrs at 120° C. After incubation, the capillary was cooled to room temperature.

The capillary was then incubated in the presence of a buffer solution comprising a conjugate of Cephapirin-Bovine Serum Albumin (BSA) conjugate. The Cephapirin-BSA conjugate was prepared as follows. 65 mg Cephapirin, 46 mg EDC (1-ethyl-3-(3-dimethylaminopropyl)-carbodiimide) and 26 mg of N-HS (N-hydroxysuccinimide) were combined in a 16×100 mm glass tube. 1 ml DMF (N,N dimethylformamide) was added to the tube and the contents of the tube were stirred at room temperature for 30 min. 100 mg BSA was dissolved in 3 ml 20 mM potassium phosphate buffer, pH 7.2, in a separate 16×100 glass tube. The Cephapirin solution was combined with the BSA solution and stirred at room temperature for 1 hour. The Cephapirin-BSA conjugate was purified with a gel filtration column (Sephadex G-25) using 20 mM potassium phosphate buffer, pH 7.2, as the equilibration and elution buffer. The capillaries were incubated was in the resultant Cephapirin-BSA conjugate for 3 hours, during which time the Cephapirin-BSA conjugate became bound to the capillary surface. After incubation, the capillary was washed with distilled water and dried under a stream of air.

The capillary was then incubated at 25° C. for 2 hrs in a blocking solution of 10% sucrose, 0.1% bovine serum albumin and 0.05% proclin 300 in order to block any free binding sites of the capillary surface not occupied by the antibody. After incubating the capillary in the blocking solution, the capillary was washed with distilled water and dried under a stream of air.

EXAMPLE 2

Preparation of Anti-Cephapirin-CY-5® Conjugate 1 mg of activated CY-5® dye (Biological Detector Systems) dissolved in 0.2 ml of 20 mM potassium phosphate buffer, pH 7.2 was combined with 2 ml of a Cephapirin antibody solution (4 mg/ml Cephapirin antibody in 20 mM potassium phosphate buffer at pH 7.2). CY-5® dye/Cephapirin solution was then stirred at room temperature for 1 hour. The resultant CY-5®-Cephapirin conjugate was purified on a gel filtration column (SEPHADEX® G-25), where 20 mM potassium phosphate buffer, pH 7.2, was used as both the equilibration and elution buffer.

EXAMPLE 3

Assay of Milk Suspected of Comprising Cephapirin

About 4 to 5 µl of antibody conjugate solution, as prepared in Example 2, was added to 0.5 ml of milk suspected of comprising cephapirin, resulting in an overall conjugate concentration in the milk of 10 µg/ml. The milk conjugate mixture was then incubated for a few seconds.

One end of the prepared capillary from Example 1 was dipped into the incubated milk. A 10 µl plug of milk was taken up into the capillary under capillary force.

The capillary was then turned upside down so that the 10 µl plug of liquid moved down the capillary into a region in which the outer surface of the capillary had not contacted the milk. The sample plug was incubated in the capillary for 1 min to allow the reaction to proceed to provide a detectable fluorescent signal for a positive sample.

The plug was then washed from the capillary with 100 µl of distilled water. After washing the capillary, the capillary was dried with a stream of air from an air gun.

The capillary was then irradiated with a laser, where the wavelength of light from the laser was 632.8 nm. Upon irradiation, an highly intense emitted signal having a wavelength of 667 nm was detected. The intensity of the emitted signal indicated that no cephapirin was present in the assayed milk.

It is evident from the above examples and discussion that improved immunoassay methods of analyte detection in capillaries are provided, where a fluorescently labeled conjugate is employed. The subject method provides reliable results in short periods of time by assaying small sample volumes. The subject method requires fewer procedural steps than other immunoassay methods conducted in capillary containers. The subject method is adaptable for use with a wide variety of samples and analytes. Finally, untrained operators may practice the subject method successfully.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An immunoassay method for detecting an analyte in a liquid sample, said method comprising steps of:
    providing a first specific binding pair member conjugated to a fluorescent label;
    providing a translucent capillary having an inner diameter of from about 0.1 µm to 1.0 mm comprising in a detection region a second specific binding pair member, wherein said first specific binding pair member is capable of: (a) competing with said analyte for binding to said second specific binding pair member or (b) concomitantly binding with said second specific binding pair member to said analyte;
    combining said sample with said first member and said second member, whereby said first member binds to said second member in relation to the amount of said analyte in said sample in said detection region, wherein said sample contacts less than 30% of the length of the outer surface of said capillary;
    washing away any first member in said capillary not specifically bound to said second member;
    irradiating said detection region from a location external to the diameter of the capillary; and
    detecting the amount of fluorescence passing through a wall of the capillary from said detection region as indicative of the presence of said analyte in said sample.

2. A method according to claim 1, wherein said combining comprises:
    adding said first member to said sample to provide a reaction medium; and
    taking up at least a portion of said reaction medium into the capillary, wherein said reaction medium contacts said second member in said detection region.

3. A method according to claim 2, wherein said capillary lacks said second member at a first end and said sample is taken up at said first end comprising the additional step of turning over the capillary, whereby said sample moves to said detection region.

4. A method according to claim 1, wherein said capillary is glass.

5. An immunoassay method for detecting an analyte in a liquid sample, said method comprising steps of:
    providing a first specific binding pair member which is competitive with said analyte for binding to the complementary binding member of said pair, said first member conjugated to a fluorescent label;
    providing a translucent capillary having an inner diameter of from about 0.1 µm to 1.0 mm comprising in a detection region on the internal surface of said capillary a second specific binding pair member capable of binding to said first member;
    combining said sample with said first member and said second member, whereby said first member binds to said second member in relation to the amount of said analyte in said sample in said detection region, wherein said sample contacts less than 30% of the length of the outer surface of said capillary;
    washing away any first member in said capillary not specifically bound to said second member;
    irradiating said detection region from a location external to the diameter of the capillary; and
    detecting the amount of fluorescence passing through a wall of the capillary from said detection region as indicative of the presence of said analyte in said sample.

6. A method according to claim 5, wherein said analyte is a hapten and bound in said detection region as a hapten protein conjugate.

7. A method according to claim 6, wherein said first conjugate is an antibody to said hapten.

8. A method according to claim 5, wherein said detection region is distal to a first end of said capillary and wherein said reaction medium is taken up at said first end and said capillary is inverted to move said reaction medium to said detection region.

9. A method according to claim 5, wherein said capillary is glass and the internal surface of said capillary is coated with an aminoalkylsiloxane.

10. An immunoassay method for detecting an haptenic analyte in a liquid sample, said method comprising steps of:
    providing an anti-analyte conjugated to a fluorescent label;
    providing a translucent capillary having an inner diameter of from about 0.1 µm to 1.0 mm coated internally with an aminoalkylsiloxane and comprising a capture hapten conjugated to a protein bound to said capillary internally in a reaction region;
    combining said sample with said anti-analyte to, form a reaction medium;
    taking up said reaction medium into said capillary where said anti-analyte binds to said capture hapten in relation to the amount of said haptenic analyte in said sample in said detection region, wherein said reaction medium contacts less than 30% of the length of the outer surface of said capillary;

washing away said anti-analyte in said capillary not specifically bound to said capture hapten;

irradiating said detection region from a location external to the diameter of the capillary; and detecting the amount of fluorescence passing through a wall of the capillary from said detection region, as indicative of the presence of said haptenic analyte in said sample.

11. A method according to claim 10, wherein said haptenic analyte is an antibiotic and said sample is milk.

12. A method according to claim 10, wherein said detection region is distal to a first end of said capillary and wherein said reaction medium is taken up at said first end and said capillary is inverted to move said reaction medium to said detection region.

13. A glass capillary comprising an internal coating of an aminoalkylsiloxane, a protein conjugate coated region extending from a first end only a portion of the length of said capillary and coating an external region extending from said first end not greater than said portion, wherein said protein conjugate is a hapten covalently bonded to a protein.

14. A glass capillary according to claim 13, wherein said hapten is an antibiotic.

* * * * *